United States Patent [19]

Doel et al.

[11] Patent Number: 5,833,958
[45] Date of Patent: Nov. 10, 1998

[54] DENTIFRICE COMPOSITIONS

[75] Inventors: Geoffrey Royston Doel, Surbiton; Andrew William Smith, Beckenham, both of England

[73] Assignee: AMBI Inc., Tarrytown, N.Y.

[21] Appl. No.: 244,846

[22] PCT Filed: Dec. 17, 1992

[86] PCT No.: PCT/GB92/02348

§ 371 Date: Jun. 15, 1994

§ 102(e) Date: Jun. 15, 1994

[87] PCT Pub. No.: WO93/11738

PCT Pub. Date: Jun. 24, 1993

[30] Foreign Application Priority Data

Dec. 17, 1991 [GB] United Kingdom ............ 9126686

[51] Int. Cl.$^6$ ............... A61K 7/16; A61K 7/18; A61K 7/22
[52] U.S. Cl. .............. 424/52; 424/49; 424/54
[58] Field of Search ......................... 424/49–58

[56] References Cited

U.S. PATENT DOCUMENTS

| | | | |
|---|---|---|---|
| 4,022,880 | 5/1977 | Vinson et al. | |
| 4,980,163 | 12/1990 | Blackburn et al. | 424/115 |
| 5,082,653 | 1/1992 | Pan et al. | 424/54 |
| 5,135,910 | 8/1992 | Blackburn et al. | 514/2 |
| 5,217,950 | 6/1993 | Blackburn et al. | 514/2 |
| 5,260,271 | 11/1993 | Blackburn et al. | 514/2 |

FOREIGN PATENT DOCUMENTS

| | | |
|---|---|---|
| 0 140 498 | 5/1985 | European Pat. Off. . |
| 710 129 | 6/1954 | United Kingdom . |
| 2 160 771 | 1/1986 | United Kingdom . |
| 1 063 787 | 3/1967 | WIPO . |
| 8 912 399 | 12/1989 | WIPO . |

OTHER PUBLICATIONS

Int. J. Clin. Pharm. Res. vol. 4, No. 8, 1988 pp. 259–261 Matula et al 'Salivary Levels of Gramicidin After Use A Tyrothricin–Containing Gargle/Mouth–Wash and Thyrothricin Lozenges.

Primary Examiner—Shep K. Rose
Attorney, Agent, or Firm—White & Case L.L.P.

[57] ABSTRACT

A dentifrice formulation provides a composition which contains and antibacterially effective amount of a lanthocin-type bacyeriocin antibacterial agent such as nisin, gramicidin, or tyrothicin and an orally acceptable low anion or anio-free excipient mixture containing a purified surfactant selected from nonionic surfactant, cationic surfactant and amphoteric surfactant so as to avoid anionic surfactant; a low or anion or anion-free abrasive; a nonionic thickening agent; a humectant; and a fluoride ion producing compound.

10 Claims, 1 Drawing Sheet

1

DENTIFRICE COMPOSITIONS

This is a Rule 371 of PCT/GB92/02348 filed Dec. 17, 1992. This invention relates to oral hygiene compositions and in particular to dentifrices comprising particular antibacterial agents which compositions are useful in antiplaque therapy.

Oral hygiene compositions for use in antiplaque therapy generally comprise an antibacterial agent as the antiplaque agent. Antibacterial agents already used in various oral hygiene compositions include cationic antibacterial agents such as chlorhexidine digluconate and cetyl pyridinium chloride and non-cationic antibacterial agents such as triclosan.

Another class of antibacterial agents are the bacteriocins. These have been defined as proteinaceous substances produced by bacteria and which have antibacterial activity only against species closely related to the species of origin. More recently it has been found that, at least in certain instances, the spectrum of antibacterial activity may in fact be broader.

An example of a bacteriocin which has already found commercial application is nisin. This is a lanthocin, comprising the atypical amino acid lanthionine. Nisin is a polypeptide with antibacterial properties which is produced naturally by various strains of the bacterium *Streptococcus lactis*. It is also a naturally occurring preservative found in low concentration in milk and cheese. Nisin has recently been recognised by the FDA as a direct food ingredient. A summary of nisin's properties is to be found in Advances in Applied Microbiology 27 (1981), 85–123.

Recently, a purified form of nisin has been made available by Applied Microbiology Inc under the trade name AMBICIN N. It has been suggested for use in a variety of applications including oral care, as disclosed in PCT Application WO 89/12399 to Blackburn et al., and now in issued U.S. Pat. No. 5,135,910 for use in the oral cavity. U.S. Pat. No. 5,135,910 specifically includes in the formulations of the lanthione antibacterial agents the use of all surfactants, including those which are anionic.

However, it has now been found that the bactericidal activity of the bacterocin derivatives, particularly nisin, is incompatabile with anionic surfactants. As far as we are aware, no specific proposals for a dentifrice formulation have been proposed which has recognized this particular problem.

Accordingly, the present invention provides for a dentifrice formulation which comprises an antibacterially effect amount of a bacteriocin antibacterial agent and an orally acceptable carrier or excipient which composition does not contain an anionic surfactant.

We have found that bacteriocin antibacterial agents such as nisin are incompatible with conventional dentifrice bases that contain strong anionic surfactants, such as sodium lauryl sulphate and sodium N-methyl-N-cocyl laurate which are conventionally used in such bases. It is believed that the strong anionic surfactants reversably inactivate or inhibit the bacteriocin antibacterial agents which tend to be positively charged. Care must therefore be exercised in selecting suitable surfactants for their compatibility with the antibacterial agent.

When used herein, in respect of a dentifrice ingredient, the term "compatible" is used to mean that the activity of the bacteriocin is not substantially compromised by the presence of the ingredient. Suitably that activity in the presence of the ingredient should not be less than 40%, preferably less than 50%, advantageously less than 60% of that observed in the absence of the ingredient. This may be readily checked by bioassay, for instance the zone diffusion assay described in example 4.

Suitable bacteriocin antibacterial agents include nisin, gramicidin and tyrothricin and purified forms of bacteriocins such as AMBICIN N. Nisin and in particular the purified form thereof AMBICIN N are especially preferred.

Suitably, the dentifrice comprises from 0.001 to 5.0%, preferably from 0.005 to 2.0%, advantageously from 0.02 to 1.0% of bacteriocin antibacterial agent by weight of the composition. In an alternative manner the level of baceteriocin agent needed is one which reaches a sufficent level in the oral cavity to inhibit the desired microrganisms. An effective level of a bacteriocin agent in the oral cavity, and more specifically nisin, to inhibit the desired organisms is a level of about 0.99 ppm.

When used herein, the term "orally acceptable" carrier or excipient includes the surfactant, thickening agent, humectant and abrasive, as well as other optional extras normally included in a dentifrice formulation.

Suitable surfactants for use in dentifrices according to the invention include, for instance, nonionic, cationic and amphoteric surfactants or mixtures thereof.

Suitable nonionic surfactants include, for example, polyethoxylated sorbitol esters, in particular polyethoxylated sorbitol monoesters, for instance, PEG(40) sorbitan diisostearate, and the products marketed under the trade name "Tween" by ICI; polycondensates of ethylene oxide and propylene oxide (poloxamers), for instance the products marketed under the trade name 'Pluronic' by BASF-Wyandotte; condensates of propylene glycol; polyethoxylated hydrogenated castor oil, for instance, cremophors; and sorbitan fatty esters. It is further believed that certain nonionic "Tween" products may also have better compatability with nisin than other nonionic surfactants which appear to be due to impurities present in the product. Hence, use of purified products is preferable whereever possible. Alternatively, the use of a free radical scavenger, preferably methionine may be used to remove the detrimental effects of the impurities on the bacteriocin agents.

Suitable amphoteric surfactants include, for example, long chain imidazoline derivatives such as the product marketed under the trade name 'Miranol C2M' by Miranol; long chain alkyl betaines, such as the product marketed under the tradename 'Empigen BB' by Albright+Wilson, and long chain alkyl amidoalkyl betaines, such as cocamidopropylbetaine, and mixtures thereof.

Suitable cationic surfactants include the D,L-2-pyrrolidone-5-carboxylic acid salt of ethyl-N-cocoyl-L-arginate, marketed under the trade name CAE by Ajinomoto Co. Inc., cocamidopropyl PG dimonium chloride phosphate, available under the trade name MONAQUAT PTC from Mona Corpn., and lauramidopropyl PG dimonium chloride phosphate available under the trade name MONAQUAT PTL from Mona Corpn..

Advantageously, the surfactant is present in the range 0.005 to 20%, preferably 0.1 to 10%, more preferably 0.1 to 5% by weight of the dentifrice.

Suitable thickening agents include, for instance, nonionic thickening agents such as, for example, $(C_{1-6})$alkylcellulose ethers, for instance methylcellulose; hydroxy$(C_{1-6})$ alkylcellulose ethers, for instance hydroxyethylcellulose, hydroxypropylcellulose; $(C_{2-6})$alkylene oxide modified $(C_{1-6})$alkylcellulose ethers, for instance hydroxypropyl methylcellulose; and mixtures thereof. Other suitable thickening agents include natural and synthetic gums or gum like material such as Irish Moss, gum tragacanth, sodium carboxymethylcellulose, polyvinylpyrrolidone, starch and thickening silicas. Suitably the thickening agent has decreased numbers of anionic groups, such as a carboxy group, although carboxymethyl cellulose may be used. Preferably, the thicking agent is a methyl cellulose derivative such as hydroxyethyl cellulose, or hydroxyethyl methyl cellulose.

Advantageously the thickening agent is present in the range 0.01 to 30%, preferably 0.1 to 15%, more preferbly 1 to 5%, by weight of the composition.

Suitable humectants for use in compositions of the invention include for instance, glycerine, sorbitol, propylene glycol or polyethylene glycol, or mixtures thereof; which humectant may be present in the range from 5 to 70%, preferably 5 to 30%, more preferably 10 to 30% by weight of the dentifrice. Suitably, when the nonionic thickening agent is hydroxypropyl methylcellulose, the humectant is present in up to 30% by weight of the dentifrice.

Suitable abrasives for use in compositions of the present invention include calcium carbonate, calcium phosphates, calcium pyrophosphate, insoluble sodium metaphosphate, sodium aluminosilicate, alumina, hydrated alumina, zinc orthophosphate, plastics particles and silica, of which silica is preferred. Further preferred is the use of a "low anion" silica as is described in greater detail below.

Suitable silicas include natural amorphous silicas such as for instance diatomaceous earth and synthetic amorphous silicas such as precipitated silicas and silica gels such as silica xerogels. Suitable silica xerogels are described in U.S. Pat. No. 3,538,230. Suitable grades of precipitated silicas have BET surface areas in the range 20 to 300, preferably 20 to 100 m²g and median agglomerate sizes in the range 2 to 50, preferably 5 to 30 μ.

Suitable precipitated silicas and silica xerogels are those marketed by Degussa under the trade name SIDENT and by W R Grace Corporation, Davison Chemical Division under the trade name SYLOBLANC, respectively.

Advantageously, the silica is a "low anion" silica. As used herein, the term "low-anion" silicas refers to those in which anionic impurities such as sodium sulphate and sodium silicate which normally arise during the course of the manufacturing process are kept to a minium, through careful control of the manufacturing process. "Low anion" silicas suitably have less than 1%, preferably less than 0.5% advantageously less than 0.25% by weight of anionic impurities Suitable such "low anion" silicas are described in EP 0 368 130 (Proctor & Gamble), EP 0 315 503 and EP 0 396 459 (Rhone-Poulenc) and WO 90/05113 (J. M. Huber Corp). Alternatively, grades of commercially available silica with ionic impurities may be rendered suitable by washing thereof with deionised water. Conductivity measurements on the water after washing may be used to monitor the efficacy of such washing. Suitably the conductivity of the water after washing is reduced to less than 200 μSiemens/cm. Suitable "low anion" silicas include the grade RP93 available from Rhone-Poulenc.

Suitably, compositions will have from 5 to 80%, preferably from 10 to 60% by weight of the abrasive.

In a preferred aspect, compositions according to the present invention comprise a nonionic surfactant such as, for instance, a polycondensate of ethylene oxide and propylene oxide; a nonionic thickening agent such as, for instance, hydroxypropyl methylcellulose; a humectant such as, for instance, glycerin; and an abrasive such as for instance a "low-anion" silica. In a second preferred aspect, a composition according to the present invention comprises a nonionic surfactant such as, for instance, a polycondensate of ethylene oxide and propylene oxide, a thickening agent such as sodium carboxymethyl cellulose (or hydroxy ethyl cellulose) optionally admixed with a thickening silica, a humectant such as sorbitol optionally admixed with glycerin and an abrasive such as a "low anion" silica.

Compositions according to the present invention may usefully comprise a fluoride ion source, to provide an anti-caries activity. A fluoride ion source is found to be compatible with the bacteriocin peptide antibacterial agent. Suitable fluoride ion sources include metal fluoride salts, for instance alkali metal fluoride salts such as sodium fluoride, amine fluoride salts, alkali metal monofluorophosphate salts such as sodium monofluorophosphate and amine monofluorophosphate salts. Suitably the fluoride ion source would, if present, be included to provide from 50 to 3500 ppm, preferably 100 to 2500 ppm of fluoride ions.

In addition to a humectant, compositions of the present invention may also contain further liquid such as, for instance, water, preferably deionised water.

The orally acceptable vehicle or carrier may also comprise further optional ingredients such as flavouring agents, sweetening agents, for example sodium saccharin, dyes, whitening agents, for example titanium dioxide, preservatives, antisensitivity agents such as strontium and potassium salts and anticalculus agents such as tetraalkali and dialkaliimetal pyrophosphate salts. It will be appreciated that in each instance, an optional ingredient, if included, will be compatible with the bacteriocin.

Dentifrices according to the present invention may be presented in any of the presentations as conventionally used in the art, for instance as toothpastes, toothpowders and gels.

Compositions according to the invention will have a pH which is orally acceptable and within which the antibacterial activity of the bacteriocin is not substantially compromised. Suitably, the pH is in the range 4 to 9.5, preferably in the range 4 to 6.5, more preferably between 4 and 5.5 and most preferably 5 to 5.5.

Compositions according to the invention may be prepared by conventional processes comprising admixing the ingredients together in the appropriate relative amounts in any order that is convenient and finally and if necessary adjusting the pH to the desired value.

Compositions of the present invention are effective against oral plaque bacterial and as such will be of use in antiplaque therapy.

Accordingly, in a further aspect, the present invention also provides a method of reducing or preventing the formation of dental plaque, which method comprises applying an antiplaque effective amount of a composition according to the present invention to a patient in need thereof.

The invention will now be illustrated by reference to the following examples.

EXAMPLE 1

| Toothpaste | |
|---|---|
| AMBICIN N | 0.50% |
| Glycerin | 22.00 |
| Hydroxypropyl methylcellulose | 3.40 |
| Titanium dioxide | 1.00 |
| Sodium saccharin | 0.10 |
| Poloxamer (Pluronic F108) | 2.00 |
| Flavour | 1.00 |
| Talin | 0.02 |
| Silica (RP93) | 16.00 |
| Deionised water | qs |

EXAMPLE 2

| Toothpaste | |
|---|---|
| AMBICIN N | 0.05% |
| Sorbitol (70% soln) | 20.00 |
| Glycerin | 15.00 |
| Sodium carboxymethyl cellulose | 1.20 |
| Sodium fluoride | 0.23 |
| Silica (RP 93) | 16.00 |
| Thickening silica (Sident 22) | 5.00 |
| Sodium saccharin | 0.30 |
| Poloxamer (Pluronic F108) | 2.00 |
| Deionised water | qs |

EXAMPLE 3

| Toothpaste | |
|---|---|
| AMBICIN N | 0.05% |
| Glycerin | 22.00 |
| Methocel K15 Premium | 0.20 |
| Methocel K100 Premium | 3.20 |
| Titanium dioxide | 1.00 |
| Sodium saccharin 30% soln. | 0.33 |
| Poloxamer (20% Pluronic F108 soln) | 10.00 |
| Sodium Fluoride | 0.221 |
| Flavour | 1.00 |
| 5% Talin Solution | 0.40 |
| Silica (RP 93) | 16.00 |
| Deionised water | qs |

The above noted example can be further prepared using Sodium carboxymethyl cellulose at 1.20 instead of the Methocel K15 Premium and Methocel K100 Premium.

Suitably the formulations of Examples 1 to 3 may also be prepared with increasing levels of nisin from 0.25%, 0.5%, 1.0% and 2%, respectively.

EXAMPLE 4

Biological Data

The compatibility of AMBICIN N with various types of surfactants was examined in a simple in vitro assay of antibacterial activity. Using *M. luteus* as the test organism, the activity of AMBICIN N was determined in the presence and absence of a range of surfactants, using a conventional zone diffusion assay in agar agar. The surfactants examined are shown in the table below, along with an indication of which category they belong to. The results are also presented graphically in FIG. 1. These show that whilst the antibacterial activity of AMBICIN N is substantailly diminished in the presence of an anionic surfactant such as sodium lauryl sulphate or sodium N-methyl-N-cocyl laurate, it is substantially maintained in the presence of a nonionic surfactant such as Pluronic F108, F127 and P87, Tween 80 and cremophor or as cationic surfactant such as CAE or an amphoteric surfactant such as Tegobataine.

TABLE

| Surfactant | Type | |
|---|---|---|
| Sodium lauryl sulphate | Anionic | |
| Adinol *CT95 | Anionic | *Trade mark of Croda Chemicals Ltd. |
| Pluronic *F108 | Nonionic | *Trade mark of BASF-Wyandotte |
| Pluronic *F127 | Nonionic | *Trade mark of BASF-Wyandotte |

TABLE-continued

| Surfactant | Type | |
|---|---|---|
| Pluronic *P87 | Nonionic | *Trade mark of BASF-Wyandotte |
| Tween *80 | Nonionic | *Trade mark of ICI |
| Tegobataine *FU | Amphoteric | *Trade mark of Th. Goldschmidt Ltd. |
| CAE* | Cationic | *Trade mark of Ajinomoto Co Inc |

EXAMPLE 5

Antibacterial spectrum of AMBICIN N

The antibacterial spectrum of activity of AMBICIN N (AMB N) was established by testing the compound against a range of orally important Gram negative and Gram positive bacteria in a conventional nominal inhibitory concentration (NIC) assay. The established antiplaque agents cetyl pyridinium chloride (CPC), chlorhexidine (CHX) and triclosan were included for comparison. The results are shown in the accompanying table. In all but two instances, AMBICIN N has superior activity.

TABLE

| | NIC data | | | |
|---|---|---|---|---|
| Organism | CPC (ppm) | CHX (ppm) | Triclosan (ppm) | AMB N (ppm) |
| Strep. agalactiae | 0.78 | 0.41 | 4.96 | 0.22 |
| Strep. sanguis | 2.12 | 0.86 | 0.88 | 0.23 |
| Strep. mutans | 3.10 | 3.94 | 1.11 | 0.43 |
| Strep. milleri | 4.58 | 1.58 | 1.08 | 0.14 |
| Strep. mitis | 2.23 | 1.50 | 3.94 | 0.33 |
| Strep. mitior | 1.22 | 4.55 | 4.23 | 0.05 |
| Strep. salivarius | 2.36 | 1.44 | 4.05 | 0.18 |
| Strep. pyogenes | 0.78 | 0.16 | 4.35 | 0.009 |
| Staph. aureus | 0.66 | 0.54 | 0.09 | 0.13 |
| G. vaginalis | 0.3 | 1.3 | 0.41 | 0.22 |
| Lacto odontolyticus | 0.83 | 1.88 | 7.49 | 0.02 |
| Act. odontolyticus | 1.23 | 3.37 | 3.02 | 0.12 |
| Act. israelii | 8.15 | 4.11 | 3.19 | 0.53 |
| Act. naeslundii | 4.61 | 2.01 | 1.98 | >12.8 |
| Act. actinomycetem | 1.02 | 0.53 | 1.69 | 0.02 |
| Fuso. nucleatum | 0.82 | 0.64 | 1.6 | 0.048 |
| Bact. intermedius | 4.68 | 2.49 | 3.72 | 0.91 |
| Peptostrepto. micros | 4.96 | 8.46 | 6.76 | >1.28 |
| Porph. gingivalis | 0.94 | 2.36 | 4.00 | >1.28 |
| Bact. ureolyticus | 0.56 | 0.69 | 7.65 | 0.035 |
| Candida albicans | 1.39 | 1.71 | 1.00 | >1.28 |
| Candida kefyr | 0.61 | 0.42 | 0.46 | >1.28 |
| Candida tropicalis | 0.48 | 0.98 | 0.35 | >1.28 |

EXAMPLE 6

Clinical data

In a double blind, crossover healthy volunteer study of 29 people, the toothpaste of example 1 containing AMBICIN N (0.05%) was found to give reductions in the aerobic, Steptococcal and anaerobic flora which were statistically significant compared to a similar placebo toothpaste from which AMBICIN N was omitted. The toothpastes were each used in a single brushing and the bacterial counts measured 15 minutes after brushing.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples are to be construed as merely illustrative and not a limitation on the scope of the present invention in any way. The embodiments of the invention in which an exclusive property or privilege is claimed are defined as follows.

We claim:

1. A low anion or anion-free antibacterial dentifrice composition consisting essentially of:

from 0.0001 to 5.0% by weight of a lanthocin type bacteriocin antibacterial agent as active ingredient selected from the group consisting of nisin, gramicidin, and tyrothricin; and an orally acceptable low anion or anion-free excipient mixture comprising a purified surfactant selected from the group consisting of a nonionic surfactant, a cationic surtactant and an amphoteric surfactant, so as to avoid an anionic surfactant; a low anion or anion-free abrasive; a nonionic thickening agent; a humectant; and a fluoride ion producing compound.

2. A dentifrice as claimed in claim 1 in which the surfactant is a poloxamer.

3. A dentifrice as claimed in claim 1 in which the orally acceptable carrier or excipient comprises a thickening agent selected from the group consisting of a natural gum, synthetic gum, and gum-like material.

4. A dentifrice as claimed in claim 3 in which the thickening agent is hydroxypropyl methylcellulose or sodium carboxymethylcellulose.

5. A dentifrice as claimed in claim 1 in which the abrasive is selected from the group consisting of calcium carbonate) calcium phosphates calcium pyrophosphate, insoluble sodium metaphosphate, sodium aluminosilicate, hydrated alumina, zinc orthophosphate, plastics particles and silica.

6. A dentifrice as claimed in claim 5 in which the abrasive is silica.

7. A dentifrice as claimed in claim 6 in which the silica abrasive is a low anion silica abrasive.

8. The dentifrice as claimed in claim 1 in which the lanthocin-type bacteriocin antibacterial agent is nisin.

9. The dentifrice as claimed in claim 1 having a pH in the range of 4. 5 to 9.

10. A method of preventing or treating plaque which method comprises applying an anti-plaque effective amount of a dentifrice as defined in claim 1 to a patient in need thereof.

* * * * *

UNITED STATES PATENT AND TRADEMARK OFFICE
CERTIFICATE OF CORRECTION

PATENT NO. : 5,833,958
DATED : November 10, 1998
INVENTOR(S) : Doel et al.

Page 1 of 1

It is certified that error appears in the above-identified patent and that said Letters Patent is hereby corrected as shown below:

Column 7, claim 1,
Line 10, delete "0.0001" and substitute therefor -- 0.001--.
Line 17, delete "surtactant" and substitute therefor -- surfactant --.

Column 8, claim 5,
Line 7, delete ")" and substitute therefor -- , --.
Line 8, insert a comma after "phosphates".

Column 8, claim 9,
Line 19, delete "4.5" and substitute therefor -- 4.5 --.

ABSTRACT,
Line 3, delete "bacyeriocin" and substitute therefor -- bacteriocin --.
Line 4, delete "tyrothicin" and substitute therefor -- tyrothricin --.
Line 5, delete "anio-free" and substitute therefor -- anion-free --.

Signed and Sealed this

Eleventh Day of December, 2001

Figure 1:
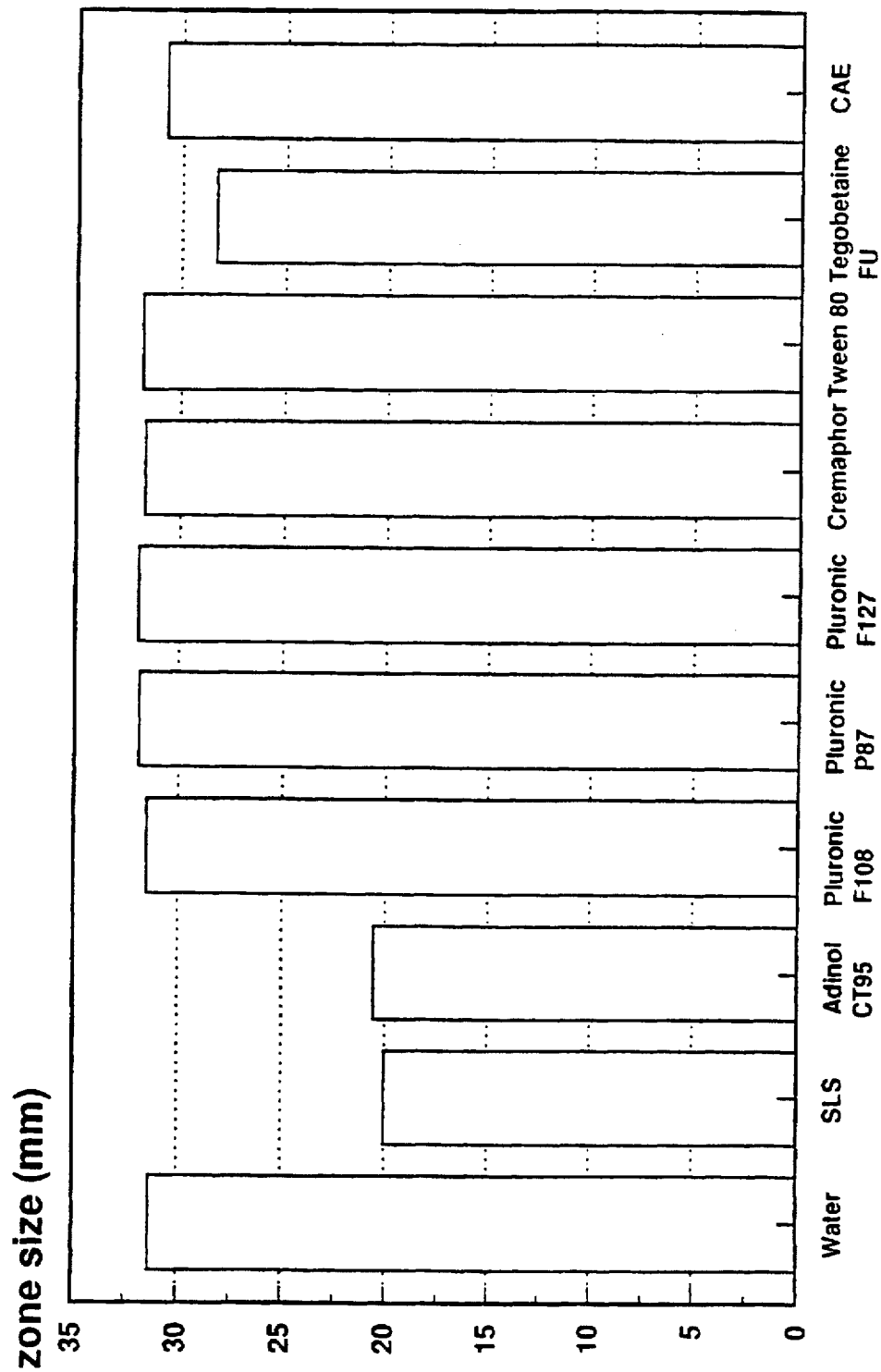

Attest:

NICHOLAS P. GODICI
Attesting Officer
Acting Director of the United States Patent and Trademark Office

UNITED STATES PATENT AND TRADEMARK OFFICE
CERTIFICATE OF CORRECTION

PATENT NO. : 5,833,958
DATED : November 10, 1998
INVENTOR(S) : Doel et al.

Page 1 of 1

It is certified that error appears in the above-identified patent and that said Letters Patent is hereby corrected as shown below:

ABSTRACT,
Line 3, delete "bacyeriocin" and substitute therefor -- bacteriocin --.
Line 4, delete "tyrothicin" and substitute therefor -- tyrothricin --.
Line 5, delete "anio-free" and substitute therefor -- anion-free --.

Column 7, claim 1,
Line 10, delete "0.0001" and substitute therefor -- 0.001--.
Line 17, delete "surtactant" and substitute therefor -- surfactant --.

Column 8, claim 5,
Line 7, delete ")" and substitute therefor -- , --.
Line 8, insert a comma after "phosphates".

Column 8, claim 9,
Line 19, delete "4.5" and substitute therefor -- 4.5 --.

Signed and Sealed this

Eighteenth Day of December, 2001

Attest:

*Attesting Officer*

JAMES E. ROGAN
*Director of the United States Patent and Trademark Office*